(12) United States Patent
Keenan

(10) Patent No.: US 7,622,172 B2
(45) Date of Patent: Nov. 24, 2009

(54) COMPOSITE FLEXIBLE AND CONDUCTIVE CATHETER ELECTRODE

(76) Inventor: Erick Keenan, 1322 Forrest Grove Rd., Vineland, NJ (US) 08360

( * ) Notice: Subject to any disclaimer, the term of this patent is extended or adjusted under 35 U.S.C. 154(b) by 396 days.

(21) Appl. No.: 11/811,182

(22) Filed: Jun. 8, 2007

(65) Prior Publication Data
US 2007/0249923 A1 Oct. 25, 2007

Related U.S. Application Data

(63) Continuation-in-part of application No. 10/367,034, filed on Feb. 19, 2003, now abandoned.

(51) Int. Cl.
*B32B 1/00* (2006.01)
*B32B 1/02* (2006.01)

(52) U.S. Cl. .................... 428/34.1; 428/35.8; 428/34.2; 428/35.7; 428/35.9; 428/36.9; 606/108; 606/190; 606/191; 606/192; 606/193; 606/194; 606/195; 606/200

(58) Field of Classification Search ................ 428/34.1, 428/35.7, 35.8, 35.9, 36.9; 606/108, 190, 606/191, 192, 193, 194, 195, 200
See application file for complete search history.

(56) References Cited

U.S. PATENT DOCUMENTS

| 2,032,256 | A | * | 2/1936 | Canfield et al. | ............. 427/309 |
| 3,316,343 | A | * | 4/1967 | Sherlock | ................... 174/84 R |
| 5,309,910 | A | * | 5/1994 | Edwards et al. | ............. 600/381 |
| 5,524,337 | A | * | 6/1996 | Houser et al. | ................. 29/825 |
| 5,871,137 | A | * | 2/1999 | Ege et al. | ..................... 228/5.7 |
| 5,871,523 | A | * | 2/1999 | Fleischman et al. | ........... 607/99 |
| 6,582,429 | B2 | * | 6/2003 | Krishnan et al. | ............. 606/41 |

* cited by examiner

*Primary Examiner*—Marc A Patterson
(74) *Attorney, Agent, or Firm*—Stuart M. Goldstein

(57) ABSTRACT

A flexible cardiac catheter for sensing electrical activity within and administering therapy to a patients' heart has a series of flexible, conductive electrode bands positioned in grooves in the catheter's tubular body. The bands consist of alternating flexible and conductive elements, providing flexibility and overall versatility to the catheter. The electrode bands have controllable flexibility due to the elastic properties of the flexible elements and continuous uninterrupted electrical current conductance from the one-piece design of the conductive element. The synergy of the components of the composite flexible and conductive bands will help solve problems current electrode bands have and will allow for a freedom in the design of catheter electrode band configurations in the future.

12 Claims, 3 Drawing Sheets

US 7,622,172 B2

COMPOSITE FLEXIBLE AND CONDUCTIVE CATHETER ELECTRODE

RELATED APPLICATION

This application is a continuation-in-part of U.S. application Ser. No. 10/367,034 filed Feb. 19, 2003, now abandoned.

BACKGROUND OF THE INVENTION

1. Field of Invention

This invention relates to the electrophysiological catheter electrode band used in the mapping (measurement of electrical potential), pacing (stimulation of the muscle tissue by pulsing an electrical current), and ablating (burning the tissue by use of high electrical current) of the heart's inner wall. This invention generally relates to catheters and leads used in sensing electrical activity within a patient and administering therapy, and more particular to such catheter and leads incorporating band electrode configured for flexibility and tractability within the body.

2. Discussion of Related Art

A method of construction of a conductive band electrode is typically now accomplished by using a rigid thin wall, metal tube (example: platinum/iridium alloy, stainless steel) band which is swaged or adhesively bonded in place and over where a conductor wire is tied onto the catheter's flexible polymer (example: PVC, polyurethane) hollow tube. This method of construction has some technical and design drawbacks. Some of these are:

1. Rigid metal bans limit catheter flexibility and make the ability of the catheter to reach a desired area impossible.

2. Rigid metal bands cannot be long in length. More than one centimeter can effect the flexibility and curve radius of the catheter, thus preventing the electrode from being placed where required.

3. Rigid metal bands have the possibility of sliding off the catheter and being lost inside the patient.

4. Pressure of the catheter flexible polymer tube and the inside wall of the band typically loosely attach the rigid metal bands to the conductor wire. Catheter flexing can then cause intermittence in the electrical signals.

5. Rigid metal bands are on the surface of the catheter's polymer tube and have corner edges which are exposed to the patient's tissue. This can cause trauma due to abrasions.

6. Rigid metal bands can also allow fluid leakage under and into the space between the band and the catheter's polymer tube. This can cause loss of signal and sterility issues.

7. Rigid metal band configuration (number and length of bands) and spacing between bands is also a problem. By trying to place bands less the one millimeter apart, difficulties are experienced in the manufacturing and performance of the catheter.

Another method of band design construction was conceived as an improvement over rigid metal bands using conductive adhesives bands (adhesives filled with a metal or other conductive powder used as the electrical conductor). This colloidal suspension matrix is flexible and thus allows for longer bands and better placement of the catheter's electrodes onto the required tissue wall; but it also has some design weaknesses:

1. The randomly dispersed conductor particles depend on a continuous touching (but not joined) to allow for the conductance of electrical current. These abutting connections can easily be broken by the curving and flexing of the catheter's polymer tube over which the conductive adhesive is applied. The resulting problems are intermittent signal and spark gap across the conductive particles.

2. Another potential problem is the loss of conductive particles into the patient's blood stream. If the adhesive bond of a band's conductive particle located at the outer surface is weak, the electrical energies conducted through the band's matrix could cause the breaking of the polymer adhesive's and conductive particle's bond and therefore liberate the particle into the patient's body.

3. Manufacturing issues are presented, such as the control of accuracy of the band's placement, the uniformity of the band's thickness, and control of the chemical science which relates to the polymer's adhesive and cohesive properties between not only the conductive particles and adhesive polymer, but also the adhesive polymer and the catheter's polymer tube.

4. Electrical current distribution could also be random and difficult to control because of the varied powder's distribution pattern throughout the inner wall, middle sections and onto the outer surface of the conductive adhesive bands.

A variation on the rigid metal band electrode is the slotted metal band electrode. The advantage of the slotted metal band is derived from several slots that are placed in a pattern around and throughout a metal band to allow flexibility. Basically this concept is still a rigid metal band and therefore many of the problems which occur in rigid metal bands still occur in the slotted metal bands, or are sometime compounded due to the slots. For example, a band's corner edges, which could cause tissue abrasions, in traditional non-slotted rigid metal bands number only two (a leading and a tailing corner edge). This problem has been increased with the slotted metal bands because of its multiple possible abrading corners. The slots also may harbor foreign matter if not thoroughly cleaned.

Unique to the prior band construction methods is a continuously wound metal wire spring coil which is wrapped around or molded into the outer surface of the catheter's distal tip and connected by a wire to transmit an electrical signal to function as an electrode. This method of band construction also gives flexibility but suffers from the need for special tooling and a higher degree of manufacturing process control. The joints between the coil loops may also harbor foreign matter if not thoroughly cleaned.

The last method compared is called thin film electrodes, which is a thin metal film that is deposited by means of vapor deposition onto the completed assembled catheter's distal tip. This metal band is flexible, but the nature of the material is such that, over time, flexing of the metal will cause stress cracks leading to band to failure. This method has some difficulties in its manufacturing process, e.g. it requires a high degree of technology and the catheter's distal tip must be completely assembled prior to the thin film application.

The above concepts have been mentioned in an attempt to give a clear contrast to the subject invention of the composite flexible conductive bands.

It also should be noted that there has been no attempt to describe the well-established process of cardiac catheter construction, so as not to distract from the focus of the invention and concept of the composite flexible and conductive band.

BRIEF SUMMARY OF THE INVENTION

The general concept of the composite flexible and conductive band is that each of its components uses their individual properties to perform a specific function and then they, with synergy, combine to meet the functional requirements of a 2 to 14 French diameter flexible conductive band electrode. The flexible (polymer/elastomer) component gives the band variable flexibility, supports the position of the conductive component, locks the conductive component safely into the band, attaches the band securely to the catheter tube, hermetically seals the conductor wire, can include a radiopaque material, and can be colored to allow for visual identification of the band or give pleasing aesthetics. The conductive component (a thin metal piece) is designed to possess an anisotrotic strength in the desired direction and not in an undesired direction, thus allowing flexibility in the required direction. The conductive component's primary functional demand is the ability to carry electrical current continuously without interruption from the connector wire onto the surface of the electrode band contacting the patient's tissue. While the previous statements describe the band components that are the mandatory base parts to accomplish a functional composite flexible and conductive electrode band, an added benefit of this invention is the ability to incorporate enhancements. Features such as a thin electroplated platinum surface onto the outside of the band is one example.

The invention of the composite flexible and conductive band succeeds over the following shortcomings and technical difficulties in some other methods of prior band design construction and manufacture for cardiac catheters. Flexibility of the electrode band and the catheter's distal tip can be better than that of the other methods, due to this invention's use of delineated functional propose. This specific use allows the utilization of the flexible component 100% for flexibility and the conductor component 100% for electrical requirements, without one component effecting the other one's functionality. Although each component performs its task independently, it is by efficient design that some components are not just neutral in a function, but aid in helping the band's performance. An example is how that the conductive component is designed to be anisotropic, so as not to impair the performance of the flexible component in its functionality.

Electrical current is uninterrupted and has no spark gaps. This is ensured by the conductive component's continuous one-piece design that connects the conductor wire and the outer surface of the electrode band without breaks or reliance on just touching.

The invention's design has a higher degree of robustness than that of some other electrode concepts. For example, the thin film metal band can flex fatigue and fail, whereas this invention places no such demands on it. Improved attachment to the catheter tube is achieved over rigid metal bands due to the fact that the bands are recessed and physically and chemically joined as one into the tube to become a single unit.

The invention has superior resistance to electrically induced polymer bond failure due to the fact the flexible component (the polymer) is not stressed into a dual role use, as the adhesive conductive bands are. The adhesive needs to act both as a tight bonding agent to attach the band onto the tube and hold onto the conductive powder, while also performing the task of an elastomer to give the band its flexibility.

This invention also allows for precise band placement control down to a space of 0.020" between conductive bands, conductive band thickness as small as 0.0005", a method of safety locking the conductive element into the band, and a hermetically seal from fluid intrusion into the catheter inner lumens.

Construction methods used to produce this invention are of a low technology in art and can be performed with simple low cost tools by technicians of moderate abilities and training. The simple design of the composite flexible and conductive electrode bands and their attachment onto a catheter lends itself to the potential for a large degree of automated tooling to produce them. Another advantageous feature of this invention is the use of economical materials which are readily available from a wide source of suppliers, in the construction of the band electrode.

The novel features which are considered as characteristic of the invention are set forth in particular in the appended claims. The invention, itself, however, both as to its design, construction and use, together with additional features and advantages thereof, are best understood upon review of the following detailed description with reference to the accompanying drawings.

DETAILED DESCRIPTION OF THE INVENTION

Figure 3:
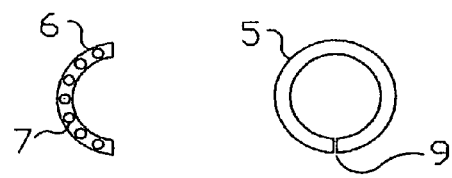
FIG. 3 shows the conductive component on the left and the flexible component on the right.
Figure 4:
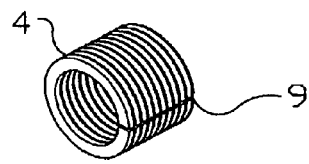
FIG. 4 shows the assembled composite flexible and conductive band in perspective.
Figure 5:
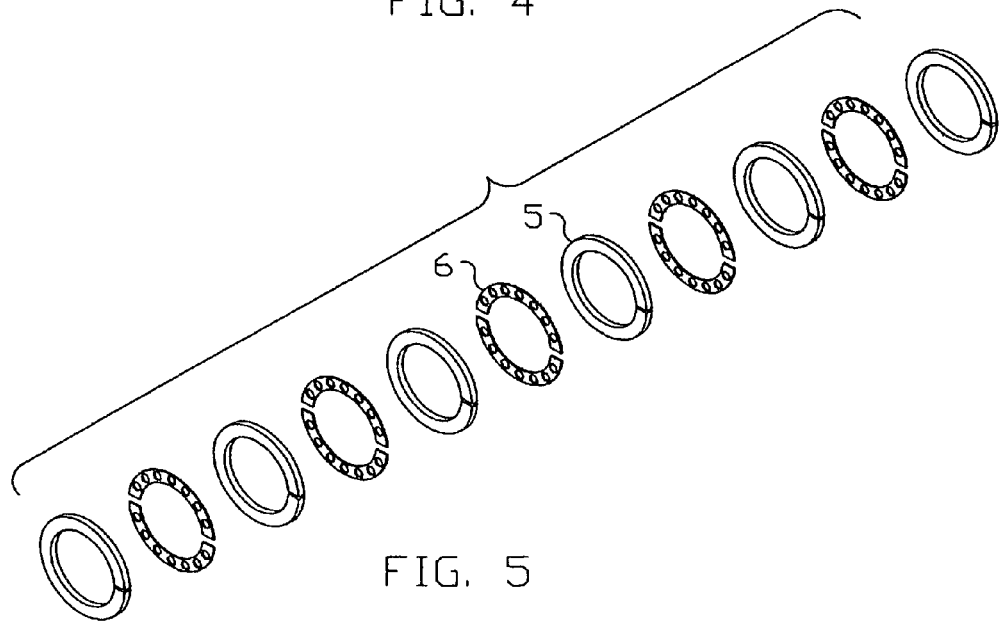
FIG. 5 shows an exploded illustration of the arrangement of components for the composite flexible and conductive bands.

FIG. 4 illustrates an assembled composite flexible and conductive electrode band 4 shown in perspective view before its assembly onto a cardiac catheter tube 1, where it performs the function of an electrode. The cylindrically shaped band 4 is a composite composed of flexible, ring shaped elements 5 and of ring shaped conductive elements 6, which are shown in FIG. 3. These component elements are arranged in an alternating pattern of flexible elements 5 and conductive elements 6 in the manner as shown in the exploded perspective illustration in FIG. 5. Uninterrupted electrical currents are carried from inside hole 8 through the wall in wire groove 2 to the outside surface of the band 4 by means of conductive element 6. Conductive element 6 is made from a thin metal (examples are gold, platinum, silver, stainless steel, platinum/iridium alloy, plated cooper or other suitable metal) sheet between 0.0005"-0.150" in thickness, from which the shape that is shown in FIG. 3 is die stamped, laser cut or produced by any other effective and equivalent method. Flexible element 5 is made from a thermoplastic polymer/elastomer which may be a polyurethane, PVC or other suitable thermoplastic polymer/elastomer from which the shape show in FIG. 3 is die stamped, laser cut, molded or produced by other effective and equivalent method. Also the polymer/elastomer used for the flexible element 6 can have compounded into it a radiopaque agent material and/or colorant which are suitable to satisfy the specification of the use of band 4.

The construction of band 4 starts with the making of the component parts. The flexible and conductive elements 5 and 6 are produced in the required number from the materials and by the method as described above. An alternating pattern of component parts are arranged in a stack. The first and the last ends are always flexible elements 5, with as many conductive elements 6 and flexible elements 5 pairs required for the length, see FIG. 5 for illustration. The stacked assembly is placed onto a round rod and loaded into a heated press. A ram presses the stack down and squeezes the assembly until a predetermined dimension is obtained. Under the influence of the pressure of the ram and the temperature that is held around the polymer's material softening point, a flowing of polymer through the link holes 7 will occur. The link holes 7 through conductive element 6 produce areas in which each abutting flexible element 5 can melt together, making all flexible elements 5 an unbroken piece of polymer/elastomer. After a short cooling time, the press is opened and band 4 is removed. At this point the composite flexible and conductive band 4 is ready for placement onto a catheter tube as an electrode.

Figure 1:
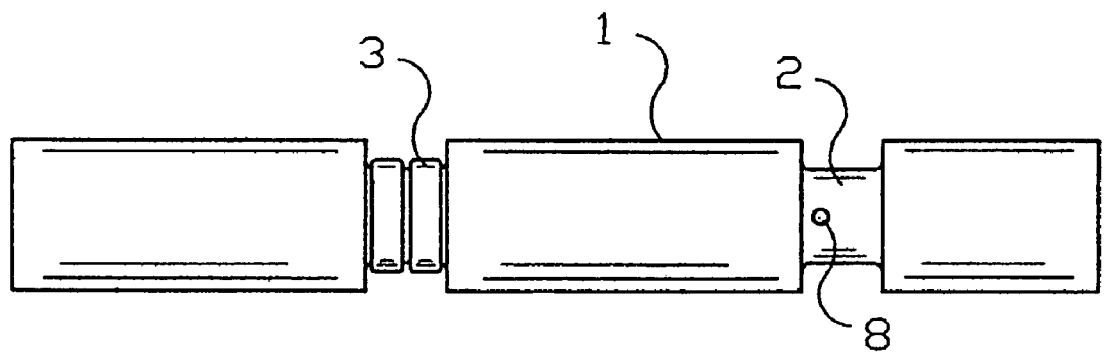
FIG. 1 shows two band grooves located at a catheter's distal tip; one on the left, which is wired, and one on the right, which is not.

For use as an electrode on a cardiac catheter, the first step is to prepare tube 1 with wire groove 2 and to wire the groove with a conductor wire 3 which will carry the electrical signal from band 4 to the proximal end of the catheter. FIG. 1 shows the deformed profile of wire groove 2 on the righthand side. The profile can be imparted into the tube 1 by either cold plastic deformation or by hot plastic deformation of the polymer tube 1.

Figure 7:
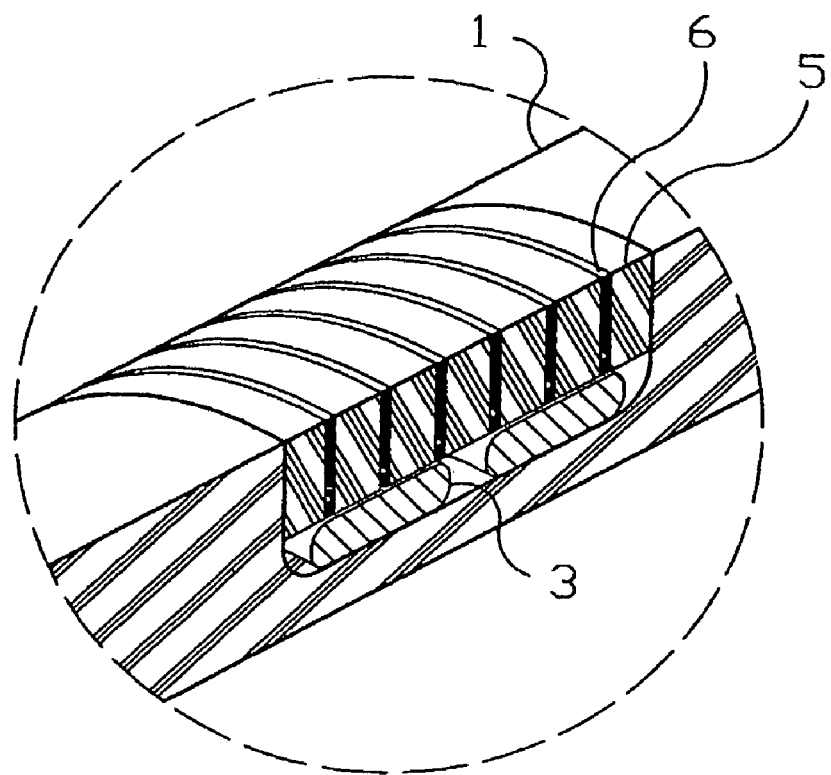
FIG. 7 shows an enlarged sectional view of a composite flexible and conductive band attached to a polymer tube.

After groove 2 has been placed where desired, a small hole 8 is punched through the wall of the recessed groove 2 area into the tube's center. A standard conductor wire 3 is stripped of its outer insulation and the exposed length is pressed into a flat shape as shown in FIG. 7; the length of stripped and pressed wire relates to the required amount of wire wrap needed. The prepared wire 3 is threaded into hole 8 with the round end first and pulled down to the end of the proximal end until the start of the flattened end starts to enter the hole. Wire 3 is then wrapped around tube 1 as shown in FIG. 1 and the area is now ready for the application of band 4.

Figure 2:
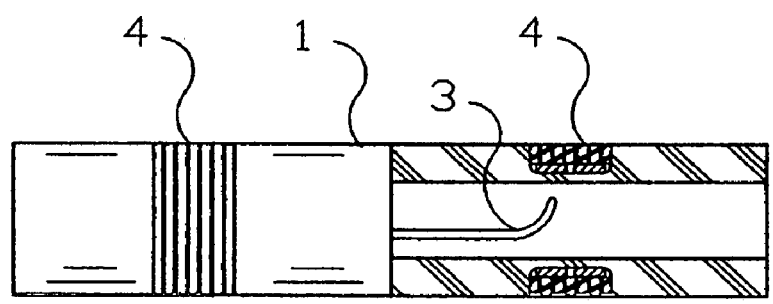
FIG. 2 shows a catheter with two composite flexible and conductive bands attached; one on the right, which is shown sectioned, and one on the left, which is not sectioned.
Figure 6:
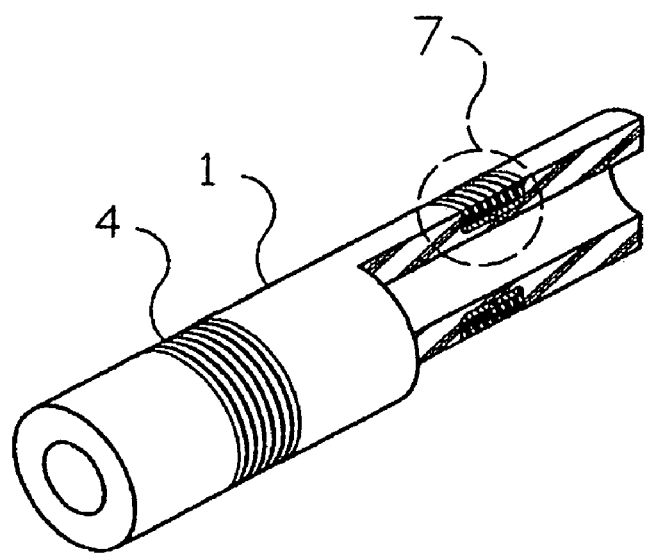
FIG. 6 shows a perspective of the polymer tube with two composite flexible and conductive bands attached; one on the right, which is shown sectioned, and one on the left, which is not sectioned.

Band 4 is opened up from small slit 9 at the six o'clock position, see FIG. 3 and FIG. 4. Like a clamshell, band 4 is then pushed over the wired area into groove 2, where it is located within and circumscribes the groove, see FIG. 2 and FIG. 6. After all the required bands 4 are in place, the assembled catheter is put into a heated mold which produces closing and sealing at slit 9 and also bonding together between tube 1 and band 4 by melting the polymers together.

Wire 3, extending through catheter tube 1, through hole 8 into groove 2, is also completely and hermetically sealed within the tube, so that it can carry electrical signals from band 4 to the proximate end of the catheter.

It is significant to note that grooves 2 formed within catheter tube 1 are critical features in the configuration of the invention. Grooves 2 permit bands 4 to be effectively locked within the grooves and hence within tube 1. This prevents dislocation of bands 4 and unwanted movement of the bands along tube 1, even during flexing movements. Ablation devices, such as disclosed in U.S. Pat. No. 5,871,523, employ wound wire on the surface of a core body. This results in slippage between the winding and body surface, thus severely limiting effective flexure of the core body. In fact, such prior art wire winding configurations, when flexed side to side, cause shearing, thus introducing tears which result in failures in any nonconductive polymer that is along the outer surface of the wire winding. Placement of the uniquely formed bands 4 into grooves 2 does not allow this movement, while permitting effective flexure movement of tube 1.

In addition, groove 2 provides an important control feature, in that it has specific dimensions which perfectly match the dimensions of band 4 (see especially FIGS. 2 and 7), to ensure that the outer diameter of catheter tube 1 is the same along its entire length, and that its outer surface is a continuously smooth surface, without sharp, abrasive edges, or uneven surfaces. Such irregular and unsafe surfaces will result from wire windings, again as disclosed in the '523 patent and similar prior art. In addition, these winding configurations have the inherent disadvantage of having abrasive "plow edges", which are also dangerous to the patient. Further, such prior art winding components will, upon any movement, result in irregularly formed, random gaps between windings that will become unwanted debris traps and pinch areas. Employing groove 2 of the present invention eliminates these significant problems.

Finally, electrical conductor wire 3 advantageously extends through hole 8, which comes through the wall of groove 2 into the center of tube 1. As a result, after band 4 is secured in position in groove 2 and wire 3 is connected, the wire is completely and hermetically sealed. Prior art configurations do not employ groove 2, and, as illustrated by the '523 patent, they must use an exposed hole in the catheter's outer surface from which to bring the conductive electrical wire to the coil windings. This hole is in an area which is prone to fluid ingression and also in an area in which the structure of the body has been weakened and therefore prone to failure.

It is therefore clear that the configuration of the present invention which employs band 4 comprising bonded elements 5 and 6 fixedly positioned within groove 2 in catheter tube 1, as fully described in detail herein, constitutes a unique catheter, which has significant advantages over the existing prior art.

Certain novel features and components of this invention are disclosed in detail in order to make the invention clear in at least one form thereof. However, it is to be clearly understood that the invention as disclosed is not necessarily limited to the exact form and details as disclosed, since it is apparent that various modifications and changes may be made without departing from the spirit of the invention.

The invention claimed is:

1. A flexible cardiac catheter for sensing electrical activity within and administering therapy to a patient's heart, said catheter comprising:
    a cardiac catheter tube with at least one groove of given width extending longitudinally along the tube and circumscribing the tube;
    at least one electrode inset within and circumscribing the groove of the tube, said electrode comprising a single, integral, unitary, cylindrically shaped, electrically conductive band, the band comprising a plurality of separate, unitary, individual, flexible elements which encircle the groove and a plurality of separate, unitary, individual, conductive elements which encircle the groove, each individual flexible element being immediately adjacent to and in contact with an individual conductive element, such that the elements are stacked and aligned transversely along the width of the groove in an alternating pattern, said electrode further comprising means to physically unite all the separate elements to form the conductive band; and
    conductor means sealed internally within the catheter tube and extending through to the groove for carrying an electrical signal from the conductive band from within the groove to a proximate end of the catheter.

2. The catheter as in claim 1 wherein the conductive band is located around and comprises part of the outer surface of the tube of the catheter.

3. The catheter as in claim 1 wherein the means to unite comprises a plurality of link holes through each of the conductive elements.

4. The catheter as in claim 1 wherein all the elements are pressed and squeezed together to form the unitary conductive band.

5. The catheter as in claim 1 wherein the flexible elements and the conductive elements are ring shaped.

6. The catheter as in claim 1 wherein the conductor means is a conductor wire.

7. The catheter as in claim 1 wherein the tube comprises more than two grooves and more than two electrodes, each electrode comprising a plurality of flexible elements and a plurality of conductive elements, each flexible element being immediately adjacent to and in contact with a conductive element, such that the elements are stacked and aligned in an alternating pattern.

8. The catheter as in claim 1 wherein the conductive elements are made of a conductive material.

9. The catheter as in claim 1 wherein the flexible elements are made of a thermal plastic polymer/elastomer.

10. The catheter as in claim 1 in which the flexible and conductive elements are pressure fitted together to form the conductive band.

11. The catheter as in claim 1 wherein each element has means for insertion onto the tube.

12. The catheter as in claim 1 wherein the means for insertion onto the tube comprises a slit.

* * * * *